US008859540B2

(12) United States Patent (10) Patent No.: US 8,859,540 B2
Rundfeldt et al. (45) Date of Patent: Oct. 14, 2014

(54) USE OF DIHYDROIMIDAZOLONES FOR THE TREATMENT OF DOGS

(75) Inventors: Chris Rundfeldt, Coswig (DE); Rita Dost, Dresden (DE); Wolfgang Loscher, Hannover (DE); Andrea Tipold, Burgdorf-Ramlingen (DE); Klaus Unverferth, Dresden (DE); Hans-Joachim Lankau, Weinbohla (DE)

(73) Assignee: Boehringer Ingelheim Vetmedica GmbH, Ingelheim (DE)

( * ) Notice: Subject to any disclaimer, the term of this patent is extended or adjusted under 35 U.S.C. 154(b) by 804 days.

(21) Appl. No.: 11/879,708

(22) Filed: Jul. 18, 2007

(65) Prior Publication Data

US 2008/0027057 A1 Jan. 31, 2008

Related U.S. Application Data

(62) Division of application No. 10/680,459, filed on Oct. 6, 2003, now abandoned.

(60) Provisional application No. 60/417,590, filed on Oct. 10, 2002.

(51) Int. Cl.
*A61K 31/535* (2006.01)
*A61K 31/41* (2006.01)

(52) U.S. Cl.
USPC ..................... 514/229.8; 514/360

(58) Field of Classification Search
USPC .............................. 514/229.8, 360
See application file for complete search history.

(56) References Cited

U.S. PATENT DOCUMENTS

| 5,869,481 | A | 2/1999 | Lankau et al. |
| 5,994,347 | A * | 11/1999 | Rostock et al. ............... 514/183 |
| 7,932,273 | B2 | 4/2011 | Schmid et al. |
| 2005/0070537 | A1 | 3/2005 | Rundfeldt et al. |
| 2005/0234104 | A1 | 10/2005 | Schmid et al. |
| 2008/0027057 | A1 | 1/2008 | Rundfeldt et al. |

FOREIGN PATENT DOCUMENTS

| CA | 2 476 054 C | 11/2011 |
| CN | 1638771 A | 7/2005 |
| CN | 1845917 A | 10/2006 |
| EP | 1 074 252 A2 | 2/2001 |
| WO | 99/00346 A1 | 1/1999 |

OTHER PUBLICATIONS

Rostock et al. "AWD 131-138 as anxiolytic anticonvulsant", Drugs of the Future, Barcelona, ES, vol. 23, No. 3, pp. 253-255, 1998.*
Bailer, et al. Progress report on new antiepileptic drugs: a summary of the fourth Eilat conference (EILAT IV), *Epilepsy Res.* 34 (1999), pp. 1-41.
Belzung, et al. "Measuring normal and pathological anxiety-like behaviour in mice: a review", Behavioural Brain Research, 125 (2001), pp. 141-149.
Hogg, Sandy "A Review of the Validity and Variability of the Elevated Plus-Maze as an Animal Model of Anxiety", Pharmacology Biochemistry and Behavior, vol. 54, No. 1, (1996), pp. 21-30.
Rodgers, et al. "Animal models of anxiety: an ethological perspective", Braz. J. Med. Biol. Res., 30(3), (1997), pp. 289-304.
Shekhar, et al. "Summary of a National Institute of Mental Health workshop: developing animal models of anxiety disorders", Psychopharmacology, 157 (2001), pp. 327-339.
Steimer, Thierry "Animal models of anxiety disorders in rats and mice: some conceptual issues", www.dialogues-cns.org, Dialogues Clin Neurosci, 13 (2011), LLS SAS, pp. 495-506.
Berendt, et al. "Epilepsy and Seizure Classification in 63 Dogs: A Reappraisal of Veterinary Epilepsy Terminology", J. Vet. Intern. Med. 13 (1999), pp. 14-20.
Bialer, et al. "Progress report on new antiepileptic drugs: a summary of the Fifth Eilat Conference (EILAT V)", Epilepsy Research, 43 (2001), pp. 11-58.
Chapman, Astrid g. "Therapeutic prospects for novel excitatory amino acid antagonists in idiopathic generalized epilepsy" in Idiopathic generalized epilepsies: clinical, experimental and genetic aspects (1994), John Libbey & Company Ltd., pp. 463-471.
Fernandez-Guasti, et al. "Species differences in the mechanism through which the serotonergic agonists indorenate and ipsapirone produce their anxiolytic action", Psychopharmacology, 107 (1992), pp. 61-68.
French, Jacqueline A. "The Role of New Antiepileptic Drugs", Am. J. of Managed Care, vol. 7, No. 7, (2001), pp. S209-S214.
Jaggy, et al. "Idiopathic epilepsy in 125 dogs: a long-term study/ Clinical and electroencephalographic findings", J. of Small Animal Practice, 39 (1998), pp. 23-29.
Löscher, et al. "Evaluation of Epileptic Dogs as an Animal Model of Human Epilepsy", Drug. Rev. 35(1), (1985), pp. 82-87.
Löscher, Wolfgang "Critical review of current animal models of seizures and epilepsy used in the discovery and development of new antiepileptic drugs", Seizure 20 (2011), pp. 359-368.
Podell, Michael "Seizures in dogs", Veterinary Clinics of North America: Small Animal Practice, 26 (1996), pp. 779-809.
Podell, Michael "Epilepsy and Seizure Classification: A Lesson form Leonardo", J. Vet. Intern. Med. 13 (1999), pp. 3-4.
Ross, et al. "Developmental and genetic audiogenic seizure models: behavior and biological substrates", Neuroscience and Biobehavioral Reviews, 24 (2000), pp. 639-653.
Rostock, et al. "D-23129: a new anticonvulsant with a broad spectrum activity in animal models of epileptic seizures", Epilepsy Research, 23 (1996), pp. 211-223.
Schicht, et al. "Pharmacokinetics of oxcarbazepine in the dog", J. Vet. Phramacol. Therap., 19 (1996), pp. 27-31.
Schwartz-Porsche, et al. "Therapeutic efficacy of phenobarbital and primidone in canine epilepsy: a comparison", J. Vet. Phramacol. Therap., 8 (1985), pp. 113-119.

(Continued)

*Primary Examiner* — Renee Claytor
(74) *Attorney, Agent, or Firm* — Fulbright & Jaworski LLP; James R. Crawford

(57) ABSTRACT

The present invention relates to the use of substituted dihydroimidazolones, particularly [1-(4-Chlorophenyl)-4-(4-morpholinyl)-2,5-dihydro-1H-imidazol-2-one] (AWD 131-138) or a physiologically acceptable salt thereof for the treatment of epilepsy in dogs.

3 Claims, 2 Drawing Sheets

(56) References Cited

OTHER PUBLICATIONS

Segan, Scott "Absence Seizures", (2008) http://www.emedicine.com/NEURO/topic3.htm.

Skradski, et al. "A Novel Gene Causing a Mendelian Audiogenic Mouse Epilepsy", Neuron, 31 (2001), pp. 537-544.

Stables, et al. "Progress report on new antiepileptic drigs. A summary of the Second Eilat Conference", Epilepsy Resesarch, 22 (1995), pp. 235-246.

Thomas, William B. "Idiopathic Epilepsy in Dogs", Common Neurologic Problems, vol. 30, No. 1, (2000), pp. 183-206.

Unverferth, et al. "Antiepileptics", Antiepileptics, Wiley-VCH Verlag GmbH & Co. KGaA, Weinheim, (2008), pp. 1-15.

Yarrington, et al. "Sequential Neuropathology of Dogs Treated with Vigabatrin, a GABA-Transminase Inhibitor", Toxicologic Pathology, vol. 21, No. 5, (1993), pp. 480-489.

"Epilepsy/Seizures" at http://www.neurologychannel.com/common/PrintPage.php (2007).

* cited by examiner

USE OF DIHYDROIMIDAZOLONES FOR THE TREATMENT OF DOGS

This application is a divisional application of Ser. No. 10/680,459 filed Oct. 6, 2003, which claims the benefit of U.S. Provisional Patent Application No. 60/417,590 filed Oct. 10, 2002, incorporated by reference in its entirety.

The present invention relates to the use of substituted dihydroimidazolones, particularly [1-(4-chlorophenyl)-4-(4-morpholinyl)-2,5-dihydro-1H-imidazol-2-one] (AWD 131-138) or physiologically acceptable salts thereof for the treatment of epilepsy and behavioral abnormalities in dogs.

Seizure disorders are the most common intracranial diseases in humans and animals, particularly dogs and cats (OLIVER 1980, SCHWARTZ PORSCHE 1984, LÖSCHER et al. 1985, FREY 1989). In the dog as well as in man, seizure disorders have an estimated morbidity of 0.5-1% (US Department of Health, Education and Welfare 1977, JANZ 1979, LÖSCHER et al.1985, KERÄNEN and RIEKKINGEN 1988, FORRESTER et al. 1989, SRENK et al. 1994). Different synonyms for epilepsy are used, but describe sudden, excessive transient paroxysmal neuronal discharges in the cerebral cortex (LÖSCHER 1993, JAGGY and STEFFEN 1995a). Considerable progress understanding underlying mechanisms has been made. An imbalance between inhibitory (BURNHAM 1989, LÖSCHER 1989) and excitatory neurotransmitters (MCNAMARA 1988, DINGLEDINE et al. 1990) have been described (FENNER and HAAS 1989). Also altered ion channels and neurotransmitter receptor functions seem to play a significant role in the pathogenesis of epilepsy (OWENS and KRIEGSTEIN 2001).

Seizures are classified as either partial or generalized seizures with tonic, clonic or tonic clonic activity, with or without loss of consciousness (SCHWARTZ PORSCHE 1984).

Epilepsy is defined as idiopathic, when no underlying causes can be defined by clinical and pathological examinations (CUNNINGHAM 1971, DE LAHUNTA 1983, MONTGOMERY and LEE 1983, SCHWARTZ PORSCHE 1984 and CHRISMAN 1991). Symptomatic epilepsy is caused either by an intracranial lesion or an extraneural, metabolic disturbance (JAGGY and STEFFEN 1995 b and c, PODELL et al. 1995, JAGGY and HEYNOLD 1996). In dogs, idiopathic epilepsy is diagnosed in approximately 45% of cases with seizure disorders (JAGGY and STEFFEN, 1995 a and c), and in 5.3-8.0% of all dogs with diseases of the nervous system (SCHWARTZ PORSCHE 1994, BERNARDINI and JAGGY 1998). In most of the canine cases with idiopathic epilepsy generalized seizures (80-90%) are observed (SCHWARTZ PORSCHE 1984, LÖSCHER et al. 1985, BRAUND 1986, CENTER 1986, JAGGY and STEFFEN, 1995 c). However, partial seizures may occur (BREITSCHWERDT et al. 1979). Seizure activity commonly starts in dogs with idiopathic epilepsy at an age of 1 3 years (CROFT 1965, CUNNINGHAM 1971, DE LAHUNTA 1983, FORRESTER et al. 1989, OLIVER and LORENZ, 1993). In some breeds inheritance was proven (OLIVER 1987, CHRISMAN 1991, OLIVER and LORENZ, 1993, JAGGY and STEFFEN, 1995a).

In dogs only a few antiepileptic drugs can be used successfully as a life long treatment, such as phenobarbital, primidone and potassium bromide (SCHWARTZ PORSCHE 1984, FREY and SCHWARTZ PORSCHE 1985, FREY 1986, SCHWARTZ PORSCHE and JORGENS 1991, LÖSCHER 1994).

However, treatment outcome is not in all cases satisfactory. In about one third of the cases, pharmacoresistency is observed (SCHWARTZ PORSCHE et al. 1982, FREY and SCHWARTZ PORSCHE 1985, LÖSCHER et al. 1985, LÖSCHER and SCHWARTZ PORSCHE 1986, HEYNOLD et al. 1997). Furthermore, using phenobarbital respectively primidone side effects may occur such as excessive sedation, ataxia, compulsive pacing, weakness, polyphagia, polydypsia and polyuria (SCHWARTZ PORSCHE et al. 1982 and LÖSCHER 1995). An elevation of liver enzymes is frequently observed (LÖSCHER 1995). Treatment with potassium bromide can result in tiredness, anorexia, obstipation, gastritis and skin lesions (LÖSCHER 1995).

Newer antiepileptic drugs such as gabapentin or lamotrigine cannot be used for the treatment of epilepsy in dogs because of an insufficient half life (LÖSCHER 1994), even though they are capable of successfully suppressing seizures induced by convulsant toxins like pentylenetetrazol (PTZ) in dogs. A further example of such drugs is abecarnil (Loscher et al., 1990) which was shown to suppress seizures induced by PTZ but which cannot be used in the treatment of epilepsy. Thus, presently available animal models can be used to test in principle whether or not a respective drug may bear the potential to become an anticonvulsant, such tests however cannot predict the clinical efficacy of the drug. The problem of short half-life is even further aggravated by the fact that the gut passage in dogs is faster than in man.

Currently a clinical study is under way to test the antiepileptic activity of phenytoin, one of the oldest anticonvulsants, administered in a sustained release formulation. A further clinical study in dogs was performed using vigabatrin (Speciale et al., 1991). This compound was selected due to its mechanism of action. The mechanism of action involves irreversible inhibition of the metabolic pathway of gamma aminobutyric acid. Thus, due to the irreversible nature or the mechanism, this drug was expected to exert its activity independent of the presence of a long half life. Single high doses were known to irreversibly block the metabolic degradation of gamma aminobutyric acid. However, this study failed due to unacceptable side effects of this drug in dogs.

Based on this information, the need for new antiepileptic drugs for dogs is obvious. Such new drugs should be active in the treatment of epilepsy in dogs suffering from epilepsy (i.e. patients). Such drugs should especially be also active in dogs suffering from epilepsy which could not be treated with the available medication. In addition, such drugs should have a better side effect profile, i.e. should produce fewer side effects upon treatment.

AWD 131-138[1-(4 chlorophenyl)-4-(4-morholinyl) 2,5 dihydro-1H-imida-zol 2-one] is a new drug with anticonvulsant and anxiolytic effects (Rostock et al., 1998a d). The drug was also shown to elevate the chemically induced seizure threshold in the intravenous pentylenetetrazol (PTZ) seizure test in mice and dogs. In dogs, 20 and 40 mg/kg p.o. increased the seizure threshold by 39 and 118%, respectively (Bialer et al., 1999). However, as disclosed above, this model is not a predictor of clinical activity of a drug in dogs suffering from epilepsy. In this PTZ test drugs are administered orally and at a defined time point after drug administration, PTZ is infused i.v. until induction of first seizure like clonic twitches. The dose of PTZ needed to induce such twitches, scaled to the body weight, is defined as convulsive threshold. Drug effects are evaluated comparing the convulsive threshold in drug treated animals with the threshold of control experiments with vehicle treatment only. The drug effect is expressed as percent increase of convulsive threshold. While this is a model indicating some activity on seizure like behavior, PTZ does not induce epilepsy in dogs limiting the predictivity of such models for diseased animals. Furthermore, due to the strict correlation between test drug administration and infusion of PTZ, the data do not indicate whether the test drug may produce sufficiently long lasting plasma levels to protect the animal from seizures over the day if administered not more than one to three times a day.

The mechanism of action of AWD 131-138 is not fully understood until now. A very low affinity for the benzodiazepine binding site of the GABAA receptor was found in a broad receptor screen. Electrophysiological studies using different cloned human GABA receptor complexes indicate that AWD 131-138 acts as a low affinity partial agonist at the benzodiazepine receptor without subtype selectivity. The maximal stimulation obtained with AWD 131-138 reached only 20% of the effect of diazepam. The specific receptor antagonist flumazenil was used to assess the contribution of the benzodiazepine receptor interaction for the pharmacological activity. The anticonvulsive activity of AWD 131-138 could be partly antagonised, and the anxiolytic activity was fully antagonised upon co administration of flumazenil. The extent of the antagonism in the seizure and anxiety test was comparable with the effect of flumazenil on the anticonvulsive and anxiolytic activity of diazepam. These data indicate that, despite the low affinity and the low intrinsic activity, the interaction of AWD 131-138 with the benzodiazepine receptor may be the main mechanism of the pharmacological activity. However, the psychopharmacological profile of AWD 131-138 differs considerably from known benzodiazepine agonists. In a drug discrimination study, monkeys did not identify AWD 131-138 as benzodiazepine like, as they did with midazolam and diazepam. This lack of benzodiazepine like psychopharmacology was also substantiated in a self administration paradigm where AWD 131-138, unlike full benzodiazepine agonists, did not substitute for cocaine. This lack of benzodiazepine like psychopharmacology may be related to the partial agonistic activity with low intrinsic activity. AWD 131-138 was also found to have weak calcium channel blocking effect. This mechanism may contribute to the anticonvulsant activity (Rostock et al., 1998a d; Rundfeldt et al. 1998; Sigel et al., 1998; Yasar et al., 1999).

In the study underlying the present invention, the efficacy of AWD 131-138 was evaluated in a clinical trial in epileptic dogs. More particularly, dogs with newly diagnosed idiopathic epilepsy without any pretreatment and dogs with idiopathic epilepsy, which did not responds to conventional antiepileptic medication where treated. Further, a combination treatment with AWD 131-138 and other epileptic drugs was carried out. In addition, the side effect profile of AWD 131-138 in comparison to other antiepileptic drugs was evaluated. Surprisingly, it was found that AWD 131-138 has a high potency to suppress seizures both in newly diagnosed and drug resistant epileptic dogs. Further, AWD 131-138 is a well tolerated even for long-term administration and less side effects are observed in comparison to traditional antiepileptic drugs. Furthermore, AWD 131-138 is efficient for the treatment of behavioural abnormalities in dogs, particularly those correlating with anxiety, i.e. fear behaviour auch as unexpected aggression against men or environment.

Thus, first aspect of the present invention is the use of [1-(4-chlorophenyl)-4-(4-morpholinyl)-2,5-dihydro-1H-imidazol 2-one] (AWD 131-138) or physiologically acceptable salts thereof as an active ingredient for the manufacture of a medicament for the treatment of epilepsy in dogs. A second aspect of the invention relates to the use of AWD 131-138 or physiologically acceptable salts thereof as an active ingredient for the treatment of behavioural abnormalities in dogs.

The medicament of the present invention may be administered by any suitable route, e.g. parenteral, oral, nasal, pulmonal administration etc. For practical purposes however, oral administration is preferred.

The medicament may be administered once or several times daily, e.g. 1-5 times daily. An administration of 1-3 times daily is especially preferred. The dose of the active ingredient is a therapeutically effective dose, i.e. a dose, which is sufficient to ameliorate or eliminate epileptic symptoms and/or behavioural abnormalities. The daily dose is preferably from 1-200 mg/kg, more preferably from 5-100 mg/kg. The dose may be adapted to the need of an individual patient. The active ingredient is usually administered as a pharmaceutical composition comprising the active ingredient and pharmaceutically acceptable carriers, diluents and/or adjuvants.

The active ingredient may also be coadministered with at least one further active ingredient if desired. The further active ingredient may be selected from other antiepileptic drugs, e.g. from phenobarbital, primidone and potassium bromide.

The medicament of the present invention may be used for the treatment of any type of epilepsy, e.g. idiopathic or symptomatic epilepsy. Especially preferred is the treatment of idiopathic epilepsy, e.g. newly diagnosed idiopathic epilepsy or already established idiopathic epilepsy, particularly drug resistant epilepsy, which cannot be treated with conventional antiepileptic dogs.

The medicament of the invention may also be used for the treatment of behavioural abnormalities, particularly anxiety.

A surprising advantage in the treatment is a reduced risk of undesirable behavioural side effects such as sedation. Further, the administration of the drug does not induce liver enzyme activity and thus does not hide other concommitant diseases.

Further, the present invention shall be explained in more detail by the following figures and examples.

1. Materials and Methods 1.1. Dogs

Figure 1:
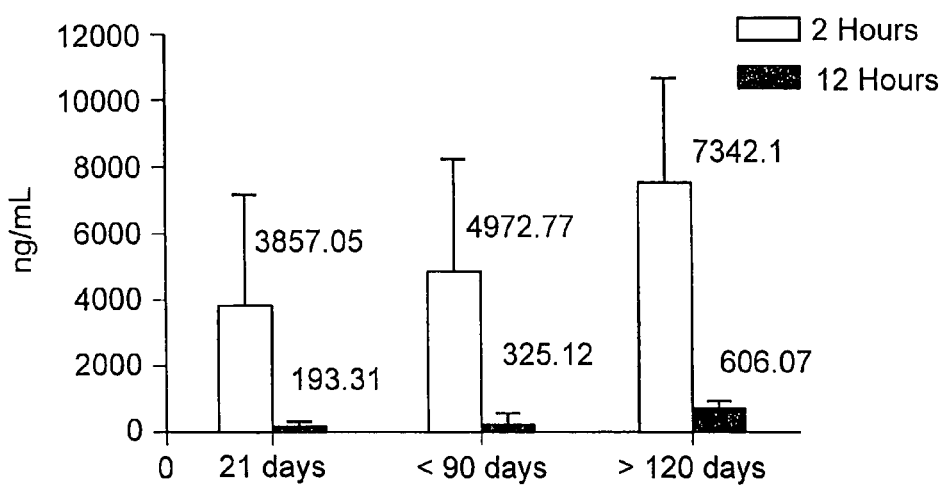
FIG. 1 shows the results of studies designed to measure plasma concentration of AWD 131-138 in subjects.

In the present study 111 dogs with idiopathic epilepsy were examined. In a prospective study 29 dogs were treated with AWD 131-138. In 12 dogs with newly diagnosed idiopathic epilepsy (newly diagnosed dogs) the initial anticonvulsant treatment was started with AWD 131-138. In further 17 dogs with chronic epilepsy and no response to conventional treatment AWD 131-138 was added (add on treatment). Retrospectively, we evaluated 82 dogs with idiopathic epilepsy. 70 newly diagnosed dogs were treated with the established antiepileptic drugs phenobarbital or primidone.

In the remaining 12 dogs with chronic epilepsy, without any improvement after treatment with these two drugs, potassium bromide was supplemented (table 1).

TABLE 1

Number of dogs included in the present study

| Treatment | number of dogs |
|---|---|
| 1. AWD 131-138 | 29 |
|    dogs with idiopathic epilepsy, newly diagnosed | 12 |
|    dogs with chronic idiopathic epilepsy phenobarbital or primidone add-on AWD 131-138 | 17 |
| 2. conventional therapy | 82 |
|    dogs with idiopathic epilepsy, newly diagnosed phenobarbital monotherapy | 44 |
|    dogs with idiopathic epilepsy, newly diagnosed primidone monotherapy | 26 |
|    dogs with chronic idiopathic epilepsy phenobarbital or primidone add-on potassium bromide | 12 |

1.1.1. Dogs: AWD 131 138 Treatment

The first part of this investigation represents a clinical pilot study testing AWD 131-138 [1-(4chlorophenyl)-4-(4morpholinyl)2,5dihydro-1H imidazol2-one]. 29 dogs with a history of seizure disorders were diagnosed with idiopathic epilepsy.

1.1.1.1. Newly Diagnosed Dogs

In twelve of these dogs idiopathic epilepsy was newly diagnosed. They were not treated prior to presentation and received a monotherapy with AWD 131-138 (table 1). One of these dogs showed after 4 months of AWD 131-138 treatment no improvement of the seizure frequency and phenobarbital (4 mg/kg body weight p.o., daily dosage) was supplemented.

All dogs had prior to the presentation two or more generalized epileptic seizures. Grand mal seizures were observed by the owners in all cases, 5 of them developed cluster of seizures. In addition to generalized seizures in 3 dogs focal seizures were observed (table 2). Seizure frequency in the 12 untreated dogs ranged from eight seizures per month to one seizure every eight months.

1.1.1.2. Dogs with Chronic Epilepsy

Seventeen dogs with chronic epilepsy had been treated with phenobarbital or primidone before presentation and did not respond to this conventional medication. The treatment period ranged from 3 months to 5 years (median 1.5 years, mean and standard deviation 1.6 1.3 years). These animals received during the pilot study a combination therapy of either phenobarbital or primidone combined with AWD 131-138 (table 1).

Eleven of these dogs were treated with daily dosages of phenobarbital from 6 to 23 mg/kg bodyweight p.o. (median 10.7, mean and standard deviation 12.9-6.6 mg/kg). Serum concentrations of phenobarbital were measured and ranged from 19.5 to 58.9 µg/mL (median 26.5, mean and standard deviation 32.0-13.6 µg/mL; reference values 15 45 µg/mL, established by FARNBACH 1984).

The remaining six dogs were treated with primidone using daily dosages from 25 to 53 mg/kg bodyweight p.o. (median 45.5, mean and standard deviation 42.8-8.9 mg/kg). In these cases phenobarbital concentration ranged from 23.2 to 27.4 µg/mL (median 23.7, mean and standard deviation 24.8 1.8 µg/mL).

Grand mal seizures were observed in all cases, 15 of them developed clusters of seizures and 8 dogs were presented with either survived or acute status epilepticus. In addition to generalized seizures in 5 dogs focal seizures and in 2 cases complex partial seizures were observed (table 2). Seizure frequency in these 17 dogs ranged from six epileptic seizures per month to one seizure every six months.

TABLE 2

Types of seizure in 29 dogs before treatment with AWD 131-138

| | number of dogs | |
|---|---|---|
| Type of seizure | newly diagnosed | chronic epilepsy |
| grand mal seizures | 12/2 | 17/17 |
| cluster | 5/12 | 15/17 |
| status epilepticus | — | 8/17 |
| focal seizures | 3/12 | 5/17 |
| complex partial seizures | — | 2/17 |

1.1.2. Dogs: Retrospective Study, Conventional Treatment

In the second part of this study, data from 82 well documented cases with idiopathic epilepsy were analyzed retrospectively.

Seventy of these dogs had a newly diagnosed idiopathic epilepsy and were untreated prior to the presentation. All dogs had two or more seizures before treatment. Forty four of these dogs were treated with phenobarbital with daily dosages ranging from 4 to 13 mg/kg bodyweight p.o. (median 5.0, mean and standard deviation 6.0 and 2.4 mg/kg). Serum concentrations ranged between 4.6 and 33.2 µg/mL (median 17.2, mean and standard deviation 18.4 and 7.2 µg/mL).

Twenty six dogs were treated with primidone and received dosages from 24 to 70 mg/kg bodyweight p.o. (median 60.0, mean and standard deviation 51.0-13.4 mg/kg). Serum concentrations of phenobarbital ranged between 5.9 and 37.5 µg/mL (median 18.3, mean and standard deviation 19.7-10.2 µg/mL).

All dogs had at least two or more seizures before treatment. In most of the dogs (n=61) generalized seizures (grand mal type) were observed. 19 dogs had clusters in the seizure history and 7 dogs were referred in the acute phase of status epilepticus or after recovery. 13 dogs had focal seizures and in 3 dogs complex partial seizures were described (table 3).

Twelve dogs with chronic epilepsy had been treated with either phenobarbital or primidone for 3 months to 3 years (median 0.5 years, mean and standard deviation 1.7-0.9 years) prior to presentation and did not respond to the medication. They received an additional drug, potassium bromide.

Eight of these dogs were treated with daily dosages of phenobarbital from 6 to 17 mg/kg bodyweight, p.o. (median 9.5, mean and standard deviation 10.0 3.2 mg/kg), serum concentrations were measured and ranged from 18.7 to 41 µg/mL (median 24.6, mean and standard deviation 27.2 to 8.4 µg/mL).

The remaining four dogs were treated with primidone at daily dosages from 50 to 70 mg/kg bodyweight p.o. (median 60.0, mean and standard deviation 60.0. 7.0 mg/kg). In these cases serum concentration ranged from 24.5 to 36.2 µg/mL (median 30.4, mean and standard deviation 30.4 to 5.9 µg/mL).

Potassium bromide was given at a daily dosage of 40-60 mg/kg bodyweight p.o. (median 41, mean and standard deviation 42.6-5.4 mg/kg). Bromide concentration ranged from 0.6 to 1.4 mg/mL (median 0.9, mean and standard deviation 1.0-0.3 mg/mL; therapeutic range 1.0-2.0 mg/mL, established by PODELL and FENNER 1993).

In all dogs generalized seizures (grand mal type) were observed. Seven dogs had clusters in the seizure history and six dogs were referred in the acute phase of status epilepticus or after recovery. Six dogs had focal seizures and in one dog complex focal seizures were described (table 3).

TABLE 3

Types of seizure in 82 dogs before treatment with phenobarbital
or primidone in dogs with newly diagnosed idiopathic epilepsy
or with chronic epilepsy (add on potassium bromide)

| Type of seizure | number of dogs | |
| --- | --- | --- |
| | newly diagnosed | chronic epilepsy |
| grand mal seizures | 61/70 | 12/12 |
| cluster | 19/70 | 7/12 |
| status epilepticus | 7/70 | 6/12 |
| focal seizures | 13/70 | 6/12 |
| Complex partial seizures | 3/70 | 1/12 |

1.2. Study Design

1.2.1. Pilot Study: AWD 131-138 Treatment

The project was designed to be a prospective study over a period of 7 to 9 months. In case of death the observation period was shorter (see results). History of the seizure frequency, severity and duration, age of onset of the first seizure and previous or ongoing antiepileptic treatment were recorded for each case (see 1.1). Epileptic seizures were categorized based on the owner's observations and video monitoring (table 2) (HEYNOLD et al. 1997, BERNARDINI and JAGGY 1998, BERENDT and GRAM 1999, THOMAS 2000).

The diagnosis of idiopathic epilepsy was based on normal physical and neurologic findings and normal special examinations. All dogs had a standardized physical and neurological examination (JAGGY and TIPOLD 1999). Bloodwork included in all cases hematology (red, white and differential cell count) and blood chemistry (alanine transferase (ALT), alkaline phosphatase (AP), glutamate dehydrogenase (GLDH), ammonia, urea, creatinine, total serum bilirubin, cholesterol, serum albumin, calcium, sodium and potassium). Plasma concentrations of phenobarbital (ALOMED, Radolfzell) were analyzed by an external laboratory. Further special examination were not performed in all dogs, but included examination of the cerebrospinal fluid, computed tomography of the skull, EEG and X ray of the thorax (table 4). In two cases idiopathic epilepsy was confirmed by histopathology.

TABLE 4

Special examinations in 29 dogs treated with AWD 131-138

| special examinations | number of dogs | |
| --- | --- | --- |
| | newly diagnosed | chronic epilepsy |
| computed tomography of the skull | 8/12 | 9/17 |
| cerebrospinal fluid | 8/12 | 9/17 |
| EEG | 8/12 | 8/17 |
| x-ray thorax | 6/12 | 6/17 |

AWD 131 138 treatment started in all cases with a dosage of 5 mg/kg bodyweight p.o. twice a day for one week. In the second week the dosage was increased to 10 mg/kg in every dog. If seizures were still observed the dosage of AWD 131-138 was increased up to 30 mg/kg bodyweight twice a day (table 5).

TABLE 5

AWD 131-138 daily dosage in mg/kg bodyweight

| | number of dogs | |
| --- | --- | --- |
| daily dosage | newly diagnosed epilepsy: AWD 131-138 monotherapy | chronic epilepsy: AWD 131-138 add on treatment |
| 20 mg/kg | 1/12 | 3/17 |
| 30 mg/kg | 4/12 | 3/17 |
| 40 mg/kg | 4/12 | 8/17 |
| 50 mg/kg | 2/12 | 2/17 |
| 60 mg/kg | 1/12 | 1/17 |

The first follow up examination was performed three weeks after therapy with AWD 131-138 was started, followed by examinations at 6 or 8 week intervals or depending on individual occurrence of seizures. A clinical and neurological examination including blood work was done. During the study all owners kept a log book with precise description of occurring seizures, including frequency, duration and severity, behavioral changes, other medication and possible observed adverse effects. At these time points the plasma concentration of AWD 131-138 and its metabolite were measured.

After the second month of treatment with AWD 131-138, a questionnaire was filled out by the owner focusing on seizure development and side effects: sedation, polyphagia, polyuria and polydipsia, vomiting, diarrhea, anorexia, attitude change, restlessness, augmented chewing after AWD application, aggressiveness toward the owner or other dogs and gait abnormalities.

1.2.1.1. Measurement of Plasma Concentration of AWD 131-138

A pharmacokinetic study was performed at the beginning of treatment in 2 dogs with 15 AWD 131-138 monotherapy and in 4 dogs with a combination therapy of AWD 131-138 and phenobarbital or primidone. All 6 dogs received 5 mg/kg bodyweight AWD 131-138. Blood was taken 3 times every 2 hours. The plasma concentration of AWD 131-138 and its metabolite were measured using HPLC/mass spectrometry. The same method was used as a compliance control during the follow up examinations. Blood was taken two and twelve hours after oral administration of AWD 131-138.

1.2.2. Retrospective Study

The data obtained in this part of the study served as control. In all 82 cases with conventional medication (see 1.1.2.) the history of seizure frequency, severity and duration, age of seizure onset and antiepileptic treatment was recorded for each case. Seizures were categorized based on the owner's observations and video monitoring.

All dogs had a standardized physical and neurologic examination (JAGGY and TIPOLD 1999). Blood work performed in all dogs included hematology and blood chemistry (see 1.2.1.). Serum concentrations of phenobarbital (ALOMED, Radolfzell) and potassium bromide (Gesellschaft fur Epilepsieforschung E.V., Bielefeld) were analyzed by standard methods. Other special examinations included computed tomography of the skull, examination of the cerebrospinal fluid, EEG and X ray of the thorax (table 6).

TABLE 6

Special examinations in 82 dogs (retrospective study)

| special examinations | number of dogs | |
|---|---|---|
| | newly diagnosed | chronic epilepsy |
| computed tomography of the skull | 22/70 | 5/12 |
| cerebrospinal fluid | 22/70 | 5/12 |
| EEG | 27/70 | 9/12 |
| x-ray thorax | 36/70 | 8/12 |

If all examinations performed were within normal limits idiopathic epilepsy was suspected, respectively diagnosed. The pet owners were asked about clinical observations, treatment outcome in respect to seizure frequency, duration and severity before and after treatment, which included a period between 1 and 9 months.

1.2.3. Statistics

The statistical software package WinSTAT for EXCEL was used to calculate descriptive parameters in each group such as mean, median value and standard deviation of age, age of seizure onset, age at the beginning of treatment, the dosages of phenobarbital or primidone including the serum concentration. The significance of differences between seizure frequency before and during treatment were calculated by the Wilcoxon Signed Rank test for paired replicates using InStat. The level of significance was chosen as P=0.05. Comparison of treatment groups were performed by ANOVA (3 groups) or Fisher's exact test (2 groups).

2. Results 2.1. Seizure Frequency
2.1.1. Pilot Study: AWD 131-138 Treatment
2.1.1.1. Newly Diagnosed Dogs Prior to presentation seizure frequency ranged from eight seizures per month to one seizure every eight months (median 1.6). During monotherapy with AWD 131 138 seizure frequency per month varied from complete control of seizures to 9 seizure events per month (median 0.71) (table 7). In 9 of these 12 dogs a seizure reduction was observed. Calculating the values in these nine dogs and therefore eliminating the non responders the median seizure frequency per month was 1.7 before treatment and 0.55 during AWD 131 138 medication. The improvement of seizure frequency in these dogs was statistically significant (p<0.05). The percentage of seizure reduction in responders was 49,8% given as mean value (table 7).

One dog (8%), which was seizuring 5 times before treatment remained seizure free for the observation period of 9 months (according to new information of the owner he is now seizure free for 17 months). A reduction of seizure frequency by more than 50% was achieved in four of twelve dogs (33%) (table 7). 3 dogs (25%) were considered as non responders defined as dogs either showing no decrease in seizure frequency or an increase in seizure frequency during treatment. One of these 3 animals died in status epilepticus 2 months after the first medication receiving a dosage of 30 mg/kg AWD 131-138 and having a measured plasma concentration of 3997.5 ng/mL 2 hours after application. One dog worsened, but improved after supplementation with phenobarbital.

Comparison of monotherapy treatment groups (2.2.1. and 2.2.2.) did not indicate any significant differences between the antiepileptic efficacy of AWD 131-138, phenobarbital or primidone, thus indicating therapeutic equivalence.

2.1.1.2. Dogs with Chronic Epilepsy and Add on Treatment with AWD 131 138

The seizure frequency per month varied during unsuccessful treatment with phenobarbital or primidone from eight seizures per month to one respectively four seizures every six months (median 1.9). During the add on treatment with AWD 131-138 seizure frequency per month ranged from free of seizures to 9 seizure events (median 2.0) (table 8). In 10 of these 17 dogs a seizure reduction was observed. Calculating the values in these ten dogs and therefore eliminating the non responders the median seizure frequency per month was 2.4 before treatment and 1.1 during supplementation with AWD 131 138. The improvement of seizure frequency in these dogs was statistically significant (p<0.05). The percentage of seizure reduction in responders was 47,2 % given as mean value (table 8).

6 dogs (35%) had a seizure reduction of more than 50%. One dog (6%) was completely free of seizures. This dog started seizuring at an age of 8½ years with 1 to 4 clusters per month. After 3 months of combined therapy with AWD 131 138 he was euthanized unfortunately because of acute leukemia. Two other dogs had still 2 seizures at the beginning of the treatment, but were free of seizures for the rest of the nine months observation period. The remaining 11 dogs had a seizure reduction under 50% (4 dogs) or were considered to be non responders (7 dogs). Nine patients in this group either died or were euthanized in status epilepticus on the owners request. Two of them were examined histopathologically. No extraneural or neural lesions were detected. Another dog died after coumarin intoxication. In these dogs the treatment observation period was reduced to 2 to 8 months.

2.1.2. Retrospective Study, Conventional Treatment
2.1.2.1. Newly Diagnosed Dogs, Phenobarbital Monotherapy Prior to treatment seizures occurred with a frequency from seven per month to one seizure every six months (median 1.6) (table 7). Seizure frequency per month during therapy with phenobarbital ranged from free of seizures to 10 seizure events (median 0.59). In 32 of these 44 dogs a seizure reduction was observed. Calculating the values in these 32 dogs and eliminating the non responders the median seizure frequency per month was 1.68 before treatment and 0.42 during the medication with phenobarbital. The improvement of seizure frequency in these dogs was statistically significant (p<0.05) using both calculations. The percentage of seizure reduction in responders was 72.4% given as mean value (table 7).

Nine (20%) out of these 44 dogs were free of epileptic seizures during the treatment. In 28 (64%) dogs a seizure reduction of more than 50% was observed. Twelve dogs (27%) were considered to be non responders. 10 dogs of these group either died or were euthanized in status epilepticus on the owners request. 3 additional dogs were euthanized because of other diseases than epilepsy.

2.1.2.2. Newly Diagnosed Dogs, Primidone Monotherapy

In these 26 dogs seizures occurred with a frequency from ten per month to one seizure every five months (median 1.75) (table 7). During primidone treatment seizure events per month ranged from 0 to 12 (median 0.39). However, this seizure reduction was not statistically significant. In 19 of 26 dogs a seizure reduction was observed. Calculating the values in these 19 dogs and eliminating the non responders the median seizure frequency per month was 2.0 before treatment and 0.29 during the medication with phenobarbital. The improvement of seizure frequency in these dogs was statistically significant (p<0.05). The percentage of seizure reduction in responders was 75.1% given as mean value (table 7).

Four dogs (15%) were free of seizures under primidone treatment. In sixteen dogs (62%) the reduction of seizure frequency was higher than 50%. Seven dogs (27%) were considered to be non responders. 10 dogs of these group either died or were euthanized in status epilepticus on the owners request.

2.1.2.3. Dogs with Chronic Epilepsy and Add on Treatment with Potassium Bromide

In twelve dogs not responding to phenobarbital or primidone medication was supplemented with potassium bromide. Seizures occurred with a frequency from 13 per month to one seizure every second month (median 3.0). During the combination therapy seizure frequency varied from 11 per month to one seizure every eight months (median 1.9) (table 8), a seizure reduction which was not statistically significant. In 7 of 12 dogs a seizure reduction was observed. Calculating the values in these 7 dogs and therefore eliminating the non responders the median seizure frequency per month was 3.0 before treatment and 0.8 during the add on treatment with potassium bromide. The improvement of seizure frequency in these dogs was statistically significant (p<0.05). The percentage of seizure reduction in responders was 59.7% given as mean value (table 8). In 5 dogs (42%) the reduction of seizure frequency was higher than 50%, 5 further dogs were considered to be non responders. 6 dogs of these group either died or were euthanized in status epilepticus on the owners request.

Comparison of treatment groups in dogs with chronic epilepsy by Fisher's exact test did not indicate any significant difference between the antiepileptic efficacy of the two add on treatment schedules, i.e. the groups with add on therapy of AWD 12 281 or potassium bromide.

TABLE 7

Effect of monotherapy with AWD 131-138, phenobarbital or primidone in epileptic dogs
Non-responders were defined as dogs either showing no decrease in seizure frequency or an increase in seizure frequency during treatment. Seizure frequencies are given as median group values, percent reduction of seizures is given as mean ± SEM (standard error of mean). "n" is the number of epileptic dogs per group. Significant differences in values before and during treatment are indicated by asterisk (P < 0.05). Comparison of treatment groups by ANOVA did not indicate any significant difference between the antiepileptic efficacy of the three drugs.

|  | AWD 131-138 | | | Phenobarbital | | | Primidone | | |
| --- | --- | --- | --- | --- | --- | --- | --- | --- | --- |
| Seizure freqency (seizures/month) | n | Before Treatment | During Treatment | n | Before Treatment | During Treatment | n | Before Treatment | During Treatment |
| All dogs | 12 | 1.6 | 0.71 | 44 | 1.6 | 0.59* | 26 | 1.75 | 0.39 |
| Without nonresponders | 9 | 1.7 | 0.55* | 32 | 1.68 | 0.42* | 19 | 2.0 | 0.29* |
| % reduction of seizures in responders | 9 | | 49.8 ± 11.3 | 32 | | 72.4 ± 4.6 | 19 | | 75.1 ± 5.1 |
| Number of dogs with >50% reduction of seizures | | | 4/12 (33%) | | | 28/44 (64%) | | | 16/26 (62%) |
| Number of seizure-free dogs | | | 1/12 (8%) | | | 9/44 (20%) | | | 4/26 (15%) |
| Number of nonresponders | | | 3/12 (25%) | | | 12/44 (27%) | | | 7/26 (27%) |

TABLE 8

Dogs with chronic epilepsy, add-on therapy with AWD 131-138 or Potassium bromide
Non-responders were defined as dogs either showing no decrease in seizure frequency or an increase i seizure frequency during treatment. Seizue frequencies are given as median group values, percent reduction of seizures is given as mean ± SEM (standard error of mean). "n" is the number of epileptic dogs per group.
Significant differences in values before and during treatment are indicated by asterisk (P < 0.05). Comparison of treatment groups by Fisher's exact test did not indicate any significant difference between the antiepileptic efficacy of the two drugs.

|  | Phenobarbital/Primidone AWD 131-138 | | | Phenobarbital/Primidone Potassium bromide | | |
| --- | --- | --- | --- | --- | --- | --- |
| Seizure freqency (seizures/month) | n | Before Treatment | During Treatment | n | Before Treatment | During Treatment |
| All dogs | 17 | 1.9 | 2.0 | 12 | 3.0 | 1.9 |
| Without nonresponders | 10 | 2.4 | 1.1* | 7 | 3.0 | 0.8* |
| % reduction of seizures in responders | 10 | | 47.2 ± 8.8 | 7 | | 59.7 ± 5.9 |
| Number of dogs with >50% reduction of seizures | | | 6/17 (35%) | | | 5/12 (42%) |
| Number of seizure-free dogs | | | 1/17 (8%) | | | 0/12 |
| Number of nonresponders | | | 6/17 (35%) | | | 5/12 (42%) |

2.2. Duration and Severity of Seizure Activity
2.2.1. Pilot Study: AWD 131-138 Treatment
2.2.1.1. Newly Diagnosed Dogs In this group of dogs the duration of the ictus prior to presentation varied from half a minute to 10 minutes (median 3.0 minutes) (table 9). The average time in most patients was 2 to 3 minutes. During monotherapy with AWD 131-138 ictus duration ranged also from half a minute to 10 minutes but with a median value of 2.5 minutes. In five cases the duration of the ictus was decreased between 12 and 50% (mean 38%). A postictal phase with behavior changes was observed in all twelve dogs before presentation and ranged between 10 minutes to 24 hours. In four dogs the postictal time was shortened for 50 to 75%.

A decrease of seizure severity was described subjectively by nine of 12 owners. Prior to presentation all dogs had grand mal seizures (table 2), which extended in five dogs to clusters. During AWD 131-138 treatment two dogs only developed focal seizures. One dog never got clusters, the other 4 dogs had a reduced seizure number per cluster (mean 45.3% reduction).

2.2.1.2. Dogs with Chronic Epilepsy and Add on Treatment with AWD 131 138

Grand mal seizure duration in seventeen dogs during the conventional monotherapy with phenobarbital or primidone ranged from 30 seconds to 10 minutes (median 2.0 minutes) (table 9). After supplementation with AWD 131 138 duration of seizures was slightly diminished from 30 seconds to 5 minutes with a median of 2.0 minutes. The time of the ictus was decreased in 3 dogs from 40 to 50%.

A postictal phase with behavior changes was observed in all dogs before presentation and ranged between 30 minutes to 48 hours (mean 8.5 hours). During AWD 131 138 treatment the range of this time was 10 minutes to 24 hours (mean 5.5 hours) since in ten dogs it was shortened for 30 to 75% (mean 54%).

In eight of seventeen cases the pet owners described subjectively a decrease of seizure severity. All seventeen dogs had prior to AWD 131 138 treatment grand mal seizures, which expanded into clusters in 15 dogs and/or into status epilepticus in 8 dogs (table 2). After additional AWD 131 138 application in nine dogs focal seizures replaced grand mal seizures partially. In three dogs clusters did not occur anymore and the number of seizures per cluster decreased in additional 4 cases between 21 and 64% (mean 39,5%). One owner reported worsening of seizure severity and stopped abruptly the application of AWD 131 138 after two months of treatment without further side effects to the dog. In another dog the AWD application was reduced gradually on the owners request after 4 months treatment without complications.

2.2.2. Retrospective Study, Conventional Treatment
2.2.2.1. Newly Diagnosed Dogs, Phenobarbital Monotherapy The duration of the ictus before treatment varied from 0.5 to 10 minutes (median 4.0 minutes) (table 9). The average time in most cases was 2 to 3 minutes. During phenobarbital application the duration of the main seizure episodes varied also from 0.5 minutes to 10 minutes but with a median value of 5.0 minutes. In only 4 dogs, which did not become seizure free, a shortening of the observed ictus from 33 to 50% occurred.

A postictal phase with behavior changes was observed in 39 dogs before treatment and ranged between ten minutes to twenty four hours (mean 3.5 hours). During phenobarbital application the postictal phase was reduced to 5 minutes to 24 hours (mean 3 hours). This time period was abbreviated in 8 dogs from 30 to 65% (mean 43%).

In 24 cases, which did not become seizure free, the owner reported subjectively a decrease of seizure severity. Before the presentation 40 dogs had grand mal seizures, which expanded in ten cases into clusters, in four dogs into status epilepticus (table 3). During phenobarbital medication in 6 dogs focal seizures instead of grand mal seizures were observed by the owner. In 3 out of ten dogs cluster development stopped. In 3 out of 4 dogs status epilepticus did not occur anymore. In 11 dogs the grand mal seizure activity remained unchanged or severity increased according to the owners record.

2.2.2.2. Newly Diagnosed Dogs, Primidone Monotherapy

In these twenty six dogs the ictus prior presentation ranged from 0.5 minutes to 10 minutes (median 1.5 minutes) (table 9). In most cases the average time was 2 to 3 minutes. During primidone therapy ictus duration varied from 0.5 minutes to 10 minutes (median of 1.0 minutes) and decreased only in 2 dogs (30%).

Postictal signs were observed in twenty two dogs before presentation and ranged between 15 minutes to 48 hours (mean 5 hours). During primidone application the postictal phase lasted for 10 minutes to 48 hours (mean 4.5 hours). The duration of the postictal phase was shortened in 5 dogs from 25 to 65% (mean 40%).

In ten of 22 cases, which did not become seizure free, the owner reported subjectively a decrease of seizure severity. Before treatment 25 dogs had grand mal seizures, which expanded in nine cases into clusters, in three dogs into status epilepticus (table 3). During primidone application in 2 dogs focal seizures instead of grand mal seizures were observed by the owner. In 5 out of ten dogs the frequency of seizures per cluster was reduced between 23 and 50% (mean 37.5%). Status epilepticus was not observed anymore in all 3 dogs. In 2 dogs seizure severity increased according to the owners record.

2.2.2.3. Dogs with Chronic Epilepsy and Add on Treatment with Potassium Bromide In the twelve dogs treated with phenobarbital or primidone monotherapy ictus duration varied from 1.0 minute to 13 minutes (median 3.0 minutes) (table 9). The average time in most cases was 1 to 3 minutes. After potassium bromide supplementation the duration of the ictus varied from 1.0 minute to 10 minutes (median 2.0 minutes). The duration of the ictus decreased in 3 dogs from 40 to 50%.

Postictal signs were observed in eleven dogs before presentation and ranged between half an hour to 24 hours (mean 6.0 hours). During combination therapy with potassium bromide the postictal phase varied from 15 minutes to 24 hours (mean 5.5 hours). The duration of postictal phase was abbreviated in two dogs (50 and 75%).

In 4 of twelve cases the owner reported a decrease of seizure severity subjectively. Prior to the combination therapy all twelve dogs had grand mal seizures which developed into status epilepticus in six dogs and in seven dogs into clusters, which did not occur anymore after supplementation with potassium bromide in 6 dogs. In one dog the owner noticed an increase of seizure severity.

TABLE 9 duration of the ictus during grand mal seizure activity before and during different anticonvulsive treatment methods

| treatment | duration before treatment | duration during treatment |
|---|---|---|
| monotherapy AWD 131-138 (n = 12) | $3.0^1$ $(0.5\text{-}10)^2$ | $2.5^1$ $(0.5\text{-}10)^2$ |

TABLE 9-continued duration of the ictus during grand mal seizure activity before
and during different anticonvulsive treatment methods

| treatment | duration before treatment | duration during treatment |
|---|---|---|
| add-on therapy phenobarbital or primidone and AWD 131-138 (n = 17) | $2.0^1$ $(0.5\text{-}10)^2$ | $2.0^1$ $(0.5\text{-}5)^2$ |
| monotherapy phenobarbital (n = 44) | $4.0^1$ $(0.5\text{-}10)^2$ | $5.0^1$ $(0.5\text{-}10)^2$ |
| monotherapy primidone (n = 26) | $1.5^1$ $(0.5\text{-}10)^2$ | $1.0^1$ $(0.5\text{-}10)^2$ |
| add-on therapy phenobarbital or primidone and potassium bromide (n = 12) | $3.0^1$ $(1\text{-}13)^2$ | $2.0^1$ $(1\text{-}10)^2$ |

Table legend:
n = number of dogs; median values$^1$ and time range$^2$ expressed in minutes 2.3. Plasma Concentrations of AWD 131-138

In six dogs entering the pilot study with AWD 131-138 a pharmacokinetic study was performed. AWD 131-138 was measured in plasma samples two, four and six hours after application. The results are summarized in table 10. The initial dosage of AWD 131-138 was 5 mg/kg bodyweight p.o. in all cases.

TABLE 10

AWD 131-138 plasma concentration in ng/mL

| | Time after application | | |
|---|---|---|---|
| | 2 hours | 4 hours | 6 hours |
| AWD 131-138 monotherapy | | | |
| Dog 1 | 720.0 | 702.7 | 229.5 |
| Dog 2 | 2579.2 | 1461.0 | 709.0 |
| AWD 131-138 phenobarbital combination therapy | | | |
| Dog 3 | 23.27 | Bld | bld |
| Dog 4 | 1019.5 | 173.8 | 19.5 |
| AWD 131-138 primidone combination therapy | | | |
| Dog 5 | 1520.5 | 1021.5 | 448.1 |
| Dog 6 | 2392.3 | 2438.7 | 1289.0 |

Figure 2:
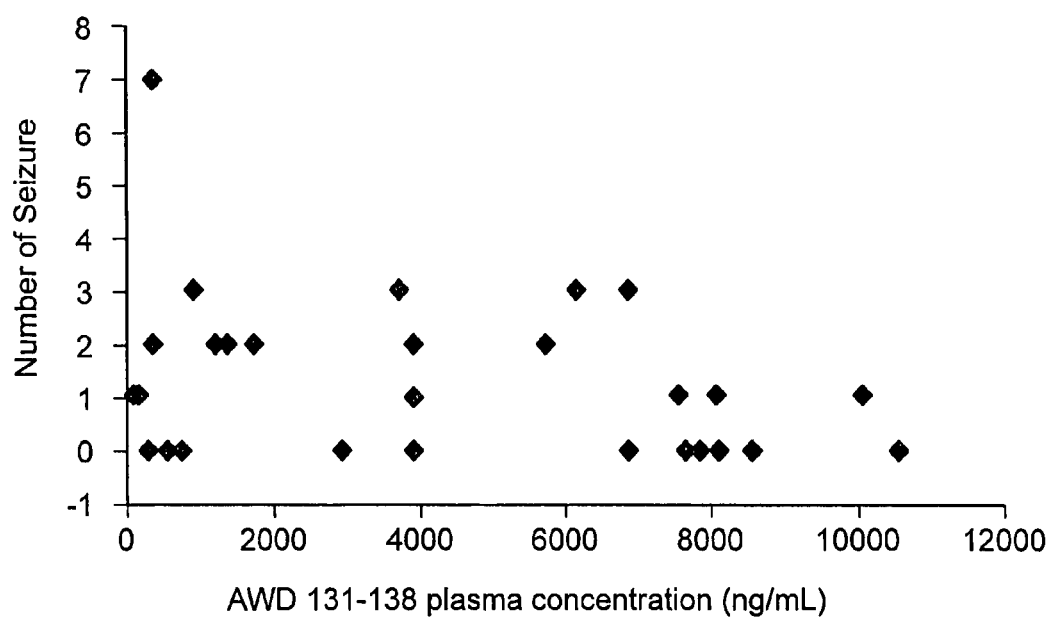
FIG. 2 also shows the results of studies designed to measure plasma concentration of AWD 131-138 in subjects.
Figure 3:
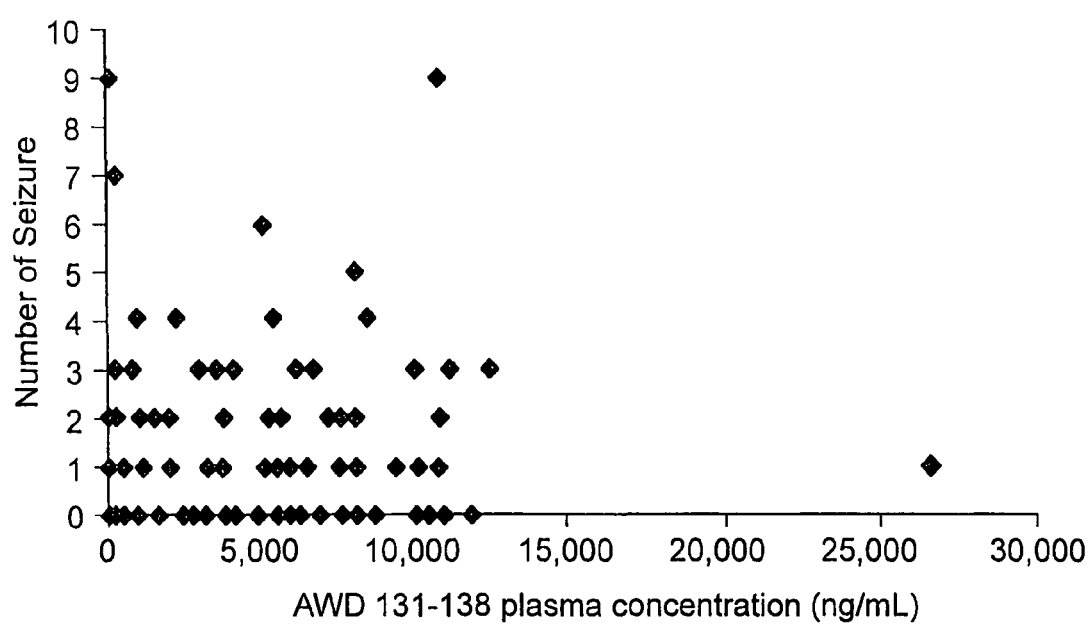
FIG. 3 graphs data relating to correlation of plasma concentration of AWD 131-138 and seizure frequency.

Table legend:
AWD 131-138: bld (below limit of detection): <2 ng/mL 2.3.1. AWD 131 138 Plasma Concentration in Newly Diagnosed Dogs To control the compliance of the owner AWD 131-138 plasma concentration were measured for the first time three weeks after the beginning of the treatment 2 and 12 hours after application. The concentration ranged in eleven cases 2 hours after oral application between 53.28 and 8619.4 ng/mL (median 2585.0, mean and standard deviation 3356.3-3290.3 ng/mL) (FIGS. 1 and 2). The AWD 131-138 dosage varied between 10 mg/kg bodyweight in eight dogs, 15 mg/kg bodyweight in two dogs and 20 mg/kg bodyweight twice a day in one dog. Plasma concentrations at this time point 12 hours after application ranged in all twelve dogs between 5.4 and 1139.2 ng/mL (median 218.1, mean and standard deviation 377.5-406.0 ng/mL) (FIG. 1). Further control examinations were performed at different time points in each dog. The plasma concentrations varied between 53.28 and 10-737.41 ng/mL two hours after oral application (FIGS. 1 and 3). There was no correlation between plasma concentration and seizure frequency (FIGS. 2 and 3).

2.3.2. AWD 131-138 Plasma Concentration in Dogs with Chronic Epilepsy

The plasma concentration of the seventeen dogs with chronic epilepsy and add on treatment ranged between 279.6 to 10613.7 ng/mL (median 2992.4, mean and standard deviation 3896.1. 3339.2 ng/mL) after 2 hours of application (FIG. 2). The AWD 131-138 dosage varied between 10 mg/kg bodyweight in fifteen dogs and 15 mg/kg bodyweight in two dogs twice a day. Plasma concentration after 12 hours of application ranged between 7.57 and 5873.04 ng/mL (median 179.3, mean 644.0). Further control examinations were also performed in this group at different time points. The plasma concentrations varied between 156.46 and 26 710.58 ng/mL two hours after oral application (FIG. 1). However, the therapeutic range of AWD 131-138 is not known until this time point. There was no correlation between plasma concentration and seizure frequency (FIGS. 2 and 3).

2.4.1 Evaluation of the Questionnaire: AWD 131-138 Application in 12 Dogs with Newly Diagnosed Idiopathic Epilepsy The treatment of dogs with AWD 131-138 was exceptionally well tolerated. The dogs remained vivid, no sedation occurred. Indeed, dogs were noticed to be even more lively and open. This slight change in behavior was especially noted in dogs known to show an anxious behavior. The main side effect in the twelve dogs treated with AWD 131 138 observed by the owners was polyphagia which occurred in 7 (58%) cases, in 4 dogs only at the beginning of the study. No further side effects were seen.

2.4.2. Evaluation of the Questionnaire: AWD 131-138 Application in 17 Dogs with Chronic Epilepsy Also in these dogs, the treatment with AWD 131-138 was very well tolerated. The main side effect observed by the owner in the seventeen dogs treated with conventional antiepileptic drugs supplemented with AWD 131-138 was polyphagia which occurred in 10 (59%) cases, in 7 dogs only at the beginning of the study. Two dogs with combined phenobarbital treatment and high levels of phenobarbital serum concentrations (56,6 58,9 µg/mL) showed ataxia in the hind limbs and apathy 2 4 hours after AWD 131-138 application with dosages from 40 mg/kg AWD 131-138 bodyweight per day and plasma concentrations from 5563.26 to 10858.45 ng/mL after 2 hours of application. In one of these dogs augmented chewing was observed after AWD application. No further side effects were seen.

2.4.3 Follow Up: AWD 131-138 Application in 12 Dogs with Newly Diagnosed Idiopathic Epilepsy During regular follow up examinations clinical and neurological examinations remained normal. One dog received from the referring veterinarian enrofloxacin because of intestinal infection and started seizuring after 24 hours. After removing this medication no further seizures were observed. No abnormalities were found in hematology (red, white and differential cell count) and blood chemistry.

2.4.4. Follow Up: AWD 131-138 Application in 17 Dogs with Chronic Epilepsy

During regular follow up examinations clinical and neurological examinations remained normal in 15 dogs. In two of the dogs with combined phenobarbital treatment the ataxia observed already by the owners could be verified. The two dogs had slight proprioceptive deficits in all 4 legs, but only 2 4 hours after AWD 131-138 application. After this time point the dogs were clinically normal. One dog received penicillin streptomycin because of pulmonary infection by the referring veterinarian and became apathic after the medication. Removing this additional medication resulted in sudden improvement.

No abnormalities were found in hematology (red, white and differential cell count). Blood chemistry revealed abnormalities already at the beginning of the study and during the add on treatment. An elevation of the AP occurred in 6 dogs, of ALT in 1 dog and of GLDH in 3 dogs. All other parameters examined remained in the normal range.

3. Discussion

AWD 131-138, a new antiepileptic and anxiolytic drug, was evaluated in this clinical pilot study in dogs with newly diagnosed or chronic idiopathic epilepsy to test the anticonvulsant effectiveness of this substance. Similar to human epilepsy animals may be selected into dogs with pharmacoresistant seizures and dogs with pharmacosensitive seizures (LÖSCHER, 1997).

In the present study the data obtained from dogs treated with AWD 131-138 were compared to results from dogs with conventional antiepileptic medication. To enter the study all dogs had to fulfill two main criterias: normal clinical and neurological examination, no abnormalities in special examinations and two or more seizures before the beginning of treatment. In dogs with chronic epilepsy the phenobarbital serum concentrations had to be in the therapeutic range. To get a broad range of epileptic dogs, animals were not selected because of breed, age, seizure type and seizure frequency. Therefore different breeds and mixed breed dogs were included. However, large breed dogs such as the German Shepherd or Retrievers were overrepresented reflecting the well known fact that large breed dogs (>15 kg) are significantly more affected with idiopathic epilepsy than small breed dogs (PODELL et al. 1995).

The majority of dogs included in all parts of the study in AWD 131-138 treatment as well as in the retrospective evaluation of conventional medication was seizuring for the first time between the first and third year of live. Several authors describe that idiopathic epilepsy mostly begins in this period (OLIVER 1987, OLIVER and LORENZ 1993, CHRISMAN 1991, DE LAHUNTA 1983, MARTIINEK et al. 1970, CROFT 1965 and 1971, CENTER 1986, CUNNINGHAM 1971, SCHWARTZ PORSCHE 1984 and FORRESTER et al. 1989). In the present study a part of the dogs started seizuring with an age younger or older than 1 to 3 years. In nearly all groups one old dog entered the study with the clinical diagnosis of idiopathic epilepsy and normal clinical and special examinations. Even the diagnosis might be questionable because of the old age, these dogs fulfilled the criteria for this study and added information to the broad aspects of a clinical pilot study.

To receive information about the ideal dosage of AWD 131-138 in naturally occurring canine idiopathic epilepsy all dogs started with 5 mg/kg bodyweight p.o. twice a day for one week. This dosage was doubled in every dog after the second week. In animals which did not respond the dosage was increased up to 30 mg/kg bodyweight p.o. twice a day. In single cases with rapid increase of the dosage no side effects were observed and it seems possible that high dosages can be used at treatment start. Different dosages modified according to the treatment response were also used in the group with conventional medication. Therefore the different treatment schedules are comparable.

Plasma concentrations of AWD 131-138 were measured for two purposes: to control pharmacokinetics after a single dose of oral application of the new substance in affected dogs and to control the owners compliance during the study. Pharmacokinetics revealed a high variation of plasma concentrations, probably caused by the different distribution of the substance in different tissues. The same variability in plasma concentrations also occurred after 3 weeks of the medication with AWD 131-138 and at different time points. An interesting finding was that in dogs with chronic epilepsy and treatment with phenobarbital supplemented with AWD 131-138 the lowest values were found. Further studies should be performed to evaluate, if a certain interaction between phenobarbital and AWD 131-138 occurs leading to low plasma concentrations. Plasma concentration did not correlate with the seizure frequency. However, in dogs with slow increase of the AWD 131-138 dosage seizure reduction occurred only with a certain delay. Since no side effects were observed a more aggressive treatment schedule could be introduced in future experiments and enhance the effectiveness in dogs with idiopathic epilepsy.

Reduction of seizure frequency using AWD 131-138 in dogs with newly diagnosed idiopathic epilepsy was comparable with the reduction in dogs treated either with phenobarbital or primidone. The results of the present retrospective evaluation of phenobarbital and primidone treatment outcome concur with previously described studies (SCHWARTZ PORSCHE et al. 1985). The three treatment groups did not indicate any significant difference between the antiepileptic efficacy of the three drugs. Calculating the reduction of the seizure frequency excluding the non responders revealed in all three groups significant differences in values before and during treatment. In the AWD 131-138 treated group total percentage of seizure reduction was somewhat lower than in the other groups. However, the number of patients in the prospective pilot study group was lower than in the retrospective group and might influence the outcome. Higher dosages of AWD 131-138 at the beginning of a treatment schedule could further improve the anticonvulsive effectiveness of the new substance.

In dogs with chronic epilepsy and add on therapy with either AWD 131-138 or potassium bromide the supplementation with another substance had an effect on the seizure frequency. Dogs improved to a similar degree in both groups. Calculating the reduction of the seizure frequency excluding the non responders revealed in both groups significant differences in values before and during treatment. The percentage of non responders was higher than in dogs with newly diagnosed epilepsy as expected.

In addition to the reduction of seizure frequency, seizure duration and severity before and during treatment was evaluated. During AWD 131-138 medication the ictus of grand mal seizures was shortened in more than $\frac{1}{3}$ of the cases. This phenomenon did only rarely occur in phenobarbital treated dogs (about $\frac{1}{10}$ of the dogs). In contrary, in phenobarbital treated dogs the median values of ictus duration increased during the medication. However, the postictal phase was shortened in all groups examined. In addition to the shortening of the ictus and the postictal phase the severity of single seizure events was reduced during AWD 131-138 treatment. Grand mal seizures changed into focal seizures, the occurrence of clusters disappeared or the number of single seizures per cluster was reduced. Most of the owners described subjectively a decrease of seizure severity.

The most obvious difference between AWD 131-138 treatment and the conventional medication occurred evaluating side effects. Unwanted side effects were only rarely reported and included polyphagia at the beginning of the treatment and ataxia in two dogs with combined phenobarbital treatment and high phenobarbital serum concentrations. The described severe side effects reported in phenobarbital treatment such as polydipsia, polyphagia, excessive sedation and gait abnormalities (BUNCH et al. 1982, SCHWARTZ PORSCHE et al.

1985) did not occur. The ataxia in the mentioned dogs was probably caused by the combination with phenobarbital. The side effects of phenobarbital treatment are sometimes not acceptable for the owners and the therapy is stopped. Using AWD 131-138 the compliance of the owners was extremely good, especially because the dogs never showed any sedation. Even more, especially in dogs known for their anxious behaviour, this was improved. This can be taken as an indicator of anxiolytic activity. Chronic application of primidone and phenobarbital may lead to considerable elevation of liver enzymes (ALT, GLDH and AP) (SCHWARTZ PORSCHE et al 1985), which was not observed in dogs treated with AWD 131-138 monotherapy and is considered to be a big advantage for the interpretation of laboratory results in possibly occurring other diseases than epilepsy.

In summary the present pilot study shows for the first time that the new substance AWD 131-138 has a potent anticonvulsant effect in dogs with idiopathic epilepsy. AWD 131-138 is equipotent to conventional antiepileptic drugs such as phenobarbital or primidone. Chronic administration is well tolerated and less side effects were observed in comparison to traditional antiepileptic drugs. These positive results support the development of AWD 131-138 as an effective anti-epileptic drug for the treatment of dogs. Unexpectedly the very low affinity and partial agonistic activity to the benzodiazepine receptor translated into anticonvulsant activity with a reduced potential for side effects in patients. Further prospective studies with higher numbers of treated animals and with higher doses of AWD 131-138 at the beginning of the treatment will likely result in even better clinical efficacy without concomitant dose limiting side effects. Further more, observations form the clinical profile indicate that the drug may have in addition anxiolytic property in dogs.

REFERENCES

BARKER, J.(1973): Epilepsy in the dog a comparative approach. J. Small Animal Pract. 14, 281 289

BERENDT, M. and L. E. GRAM (1999): Epilepsy and seizure classification in 63 dogs: a reappraisal of veterinary epilepsy terminology. J. Vet. Intern. Med; 13 (1): 14 20.

BERNARDINI, M. and A. JAGGY (1998): Idiopathic epilepsy in dogs: A long term Study of 125 cases. Clinical and electroencephalographic findings. J. Small Anim. Pract. 39 (1):23 9.

Bialer M, Johannessen S I, Kupferberg H J, Levy R H, Loiseau P, Perucca E. (1999): Progress report on new antiepileptic drugs: a summary of the fourth Eilat conference (EILAT IV). Epilepsy Res. 34:1 41.

BRAUND, K. G. (1986): Clinical syndromes in Veterinary Neurology Ed Baltimore, Williams and Wilkins 159 211

BREITSCHWERDT, E. B., J. E. BREAZILE and I. J. BOADHORST (1979): Clinical and electroencephalographic findings associated with ten cases of suspected limbic epilepsy in the dog J. Am. Anim. Hosp. Assoc. 15, 37 50

BUNCH, S. E., W. L. CASLEMAN, W. E HORNBUCKLE (1982): Hepatic cirrhosis associated with long term anticonvulsant drug therapy in dogs. J. Am. Vet. Med. Assoc. 181, 357 362

BUNCH, S. E. (1986): Anticonvulsant drug therapy in companion animals In: Kirk R. W. IX ed. Current Veterinary Therapy Philadelphia: WB Saunders, 836 844

BURNHAM, W. M. (1989): The GABA hypothesis of kindling: recent assay studies. Neurosci. Biobehav. Rev. 1989, 13; 281 288

BIELFELT, S. W., H. C. REDMAN, R. O. MC CLELLAN (1971): Sire and sex related differences in rates of epileptiform seizure in a purebred beagle dog colony. Am. J. Vet. Res. 32, 2039 2048

CENTER, S. A (1986): Seizure in the dog and cat Kal. Kan. Forum 5,11 18

CHRISMAN, C. L.(1991): Seizures In: Problems in Small Animal Neurology 2nd ed. Philadephia: Lea & Febiger, 177 205

CROFT, P. G. (1965): Fits in dogs Vet. Rec. 1965, 77, 438 455

CROFT, P. G. (1971): Fits in the dog Vet. Rec. 1971, 88,118 120

CUNNIGHAM, J. G. (1971): Canine Seizure Disorders. J. Am. Vet. Med. Assoc. 158, 589 597

CHRISMAN, C. L. (1991): Seizures In: Problems in Small Animal Neurology Lea & Febiger, Philadelphia, S. 177 205

DE LAHUNTA, A. (1983): Veterinary neuroanatomy and clinical neurology 2. Auflage W. B. Saunders Comp., Philaldelphia, 326 343

DINGLEDINE, R. (1990): Dual effect of glycine on NMDA induced neurotoxicity in rat cortical cultures. J Neurosci. December;10(12):3970 6.

FARNBACH, G. C. (1984): Serum phenobarbital concentrations and efficiency of phenytoin, phenobarbital, and primidone in canine epilepsy. J Am Vet Med Assoc. 1984; 184 (9),1117 20

FENNER, W. R. and J. A. HMS (1989): Epilepsy resistance to anticonvulsant therapy Problems in Veterinary Medicine 4, 596 605

FORRESTER, S. D., D. M. BOOTHE and G. C. TROY (1989): Current concepts in the managment of canine epilepsy Compend. Contin. Educ. Pract. Vet. 11, 811 820

FREY, H. H. (1986): Use of anticonvulsants in small animals Vet. Rec. 118, 484 486

FREY, H. H. (1989): Anticonvulsant drugs used in the treatment of epilepsy. Problems Vet. Med. 1, 558 577

FREY, H. H. and D. SCHWARTZ PORSCHE (1985): Pharmakologische Grundlagen der Behandlung der Epilepsie bei Hund und Katze Tierärztl. Prax. 13, 541 549

HEYNOLD, Y., D. FAISSLER, F. STEFFEN and A. JAGGY (1997): Clinical, epidemiological and treatment results of idiopathic epilepsy in 54 labrador retrievers: a long term study. J. Small Animal. Pract. 38, 7 14

JAGGY, A., and F. STEFFEN (1995a): Epileptische Krampfanfälle beim Hund Teil I: Klassifikation, Symptomatik und Diagnose Prakt. Tierarzt, 2, 95 102

JAGGY, A., and F. STEFFEN (1995b): Epileptische Krampfanfälle beim Hund Teil II: Extrazerebrale Ursachen von Epileptischen Anfällen Prakt. Tierarzt, 3,191 204

JAGGY, A., and F. STEFFEN (1995c): Epileptische Krampfanfälle beim Hund Teil III: Intrazerebrale Ursachen, idiopathische Epilepsie und Therapie Prakt. Tierarzt, 4, 304 314

JAGGY, A., and Y. HEYNOLD (1996): Idiopathic epilepsy in the dog Schweiz Arch Tierheilkd.;138 (11) :523 31.

JAGGY, A. and A.TIPOLD (1999): Die neurologische Untersuchung beim Kleintier und beim Pferd. Opuscula Veterinaria, WAK Verlag, München.

JANZ, D. (1979): Epidemiologie und Klassifikation von Epilepsien und epileptischen Anfällen Akt. Neurol. 6,189 196

KAY, W. J. (1989): What is epilepsy? Prob. Vet. Med. 1, 495 500

KERÄNEN, T. and P. RIEKKINGEN (1988): Severe Epilepsy: Diagnostic and Epidemiological Aspects Acta. Neurol. Scand. (Suppl. 117) 57, 7 14

KNEBEL, N. G. and B. DONATH (unpublished, 1998): Details of the method and validation ASTA Medica AG, Biochemical Research.

LEVITSKI, R. E., L. A. TREPANIER (2000): Effect of timing of blood collection on serum phenobarbital concentrations in dogs with epilepsy. J. Am. Vet. Med. Assoc. 15; 217(2): 200 4

LÖSCHER, W. (1984): Genetic animal models of epilepsy as a unique resource for the evaluation of anticonvulsant drugs. A review methods findings experiment. Clin. Pharmacol. 6, 531 547

LÖSCHER, W., D. SCHWARTZ PORSCHE, and H. H. FREY (1985): Evaluation of epileptic dogs as an animal model of human epilepsy. Arzneimittelforschung, 35, 82 87

LÖSCHER, W. (1986): Experimental models for intractable epilepsy in nonprimate animal species Intractable Epilepsy: Experimental and Clinical Aspects 25 37 Eds: D. Schmidt and P. L. Morselli Raven press, New York LÖSCHER, W. and D. SCHWARTZ PORSCHE (1986): Low levels of y aminobutyric acid in cerebrospinal fluid of dogs with epilepsy. J. Neurochem. 46, 1322 1325

LÖSCHER, W. (1989): GABA and the epilepsies: Experimental and clinical considerations In: N. G. Bowery und G. Nistico (Hrsg.) GABA: Basic aspects and clinical applications Phythagora Press, Rom, 260 300

LÖSCHER, W. (1993): Basic aspects of epilepsy Current Opinion Neurol. Neurosurg. 6, 223 232

LÖSCHER, W. (1994): Neue Antiepileptika ein Fortschritt fur die Behandlung epileptischer Tiere? Kleintierprax. 39, 325 342

LÖSCHER, W. (1995): Pharmakologie des Zentralen Nervensystems: Antiepileptica In: Löscher, W., H., H., Frey: Lehrbuch der Pharmakologie und Toxikologie für die Veterinärmedizin Enke Verlag, Stuttgart, 177 181

LÖSCHER, W. (1997): Animal models of intractable epilepsy Prog. Neurobiol., 53, 239 258

Löscher W, Honack D, Scherkl R, Hashem A, Frey HH. (1990) Pharmacokinetics, anticonvulsant efficacy and adverse effects of the beta carboline abecarnil, a novel ligand for benzodiazepine receptors, after acute and chronic administration in dogs. J. Pharmacol. Exp. Ther. 255:541 548.

MARTIINEK,.Z. and F. HORAK (1970): Development of so called "genuine" epileptic seizures in dogs during emotional excitement Physiol. Bohemoslovca. 19,185 195

MCNAMARA, J.(1988): Pursuit of the mechanisms of kindling trends Neuroscience, 11, 33 36

MONTGOMERY, D. L. and A. C. LEE (1983): Brain damage in the epileptic Beagle dog. Vet Pathol. 20,160 169

OLIVER, J. E.(1980): Seizure disorders in companion animals. Compend. Contin. Educ. Pract. Vet. 1980, 2: 77 85

OLIVER, J. E (1987): Seizure disorders and narcolepsy In: Veterinary Neurology, 2 nd ed. Philadelphia: WB Saunders 285 302

OLIVER, J. E. and M. D. LORENZ (1993): Seizures and narcolepsy In: Handbook of Veterinary Neurology, 2 nd ed. Philadelphia: WB Saunders 296 313

OWENS, D.F. and A. R. KRIEGSTEIN (2001): Muturation of channels and receptors: consequences for excitability In: Brain Plasticity and Epilepsy Int. Rev. Of Neurobiol. Academic Press, Vol.45, 43 87

PALMER, A. C.(1970): Pathologic changes in the brain associated with fits in dogs. Veterinary Record, 1972, 90,167 173

PALMER, A. C. (1972): Pathological changes in the brain associated with fits in dogs Vet. Rec. 90,167 173

PODELL, M. and W. R. FENNER (1993): Bromide therapy in refractory canine idiopathic epilepsy J. Vet. Int. Med. 7, 318 327

PODELL, M., W. R. FENNER, u. J. D. POWERS, (1995): Seizure classification in dogs from nonreferral based population J. Am. Vet. Med. Assoc. 206, 1721 1728

Rostock, A.; Tober, C.; Dost, R.; Bartsch, R. Anxiolytic effects without sedation and amnesia of AWD 131 138 in animals: A comparison with diazepam and buspirone Naunyn Schmiedeberg's Arch Pharmacol 1998a; 357; Suppl. 4; R97 Spring meeting of the German Society of Pharmacology and Toxicology, 17. Mar. 19, 1998, Mainz, Germany Rostock, A.; Tober, C.; Dost, R.; Bartsch, R. AWD 131 138 is a potential novel anxiolytic without sedation and amnesia: A comparison with diazepam and buspirone Naunyn Schmiedeberg's Arch Pharmacol 1998b; 358; Suppl. 1; P35.162 13th International Congress of Pharmacology, 26. 31.7.1998, Munich, Germany Rostock, A.; Tober, C.; Dost, R.; Bartsch, R. AWD 131 138: Anxiolytic and anticonvulsant activities without side effects in animals Behavioural Pharmacology 1998c: 9; Suppl.1; S79 7th International Meeting of the European Behavioural Pharmacology Society, 2. Sep. 6, 1998, Brno, Czech Republic Rostock, A.; Tober, C.; Dost, R.; Rundfeldt, C.; Bartsch, R.; Egerland, U.; Stark, B.; Schupke, H.; Kronbach, T.; Lankau, H. J.; Unverferth, K.; Engel, J. AWD 131 138. Drugs of the Future 1998d; 23(3): 253 255

Rundfeldt, C.; Sigel, E.; Egerland, U. First insights in the mode of action of AWD 131 138: Allosteric modulation of GABA induced currents Naunyn Schmiedeberg's Arch Pharmacol 1998a; 357; Suppl. 4; R98 Spring meeting of the German Society of Pharmacology and Toxicology, 17. Mar. 19, 1998, Mainz, Germany SCHWARTZ PORSCHE, D., W. LÖSCHER and H. H. FREY (1982): Treatment of canine epilepsy with primidone J. Am. Vet. Med. Assoc. 181, 592 595

SCHWARTZ PORSCHE, D. (1984): Epilepsie Diagnose, Differentialdiagnose und Therapie Kleintierprax., 29, 67 82

SCHWARTZ PORSCHE, D., LÖSCHER, W. and H. H. FREY (1985): Therapeutic efficacy of phenobarbital and primidone in canine epilepsy: a comparsion J. Vet. Pharmacol. Ther., 8, 113 119

SCHWARTZ PORSCHE, D. and D. JÜRGENS (1991): Wirksamkeit von Bromid bei den therapieresistenten Epilepsien des Hundes Tierärztl. Prax. 19, 395 401

SCHWARTZ PORSCHE, D. (1994): Seizures In: Braund KG ed. Clinical Syndromes in Veterinary Neurology 2 nd ed. St. Louis: Mosby Year Book, 1994 234 251

Sigel, E.; Baur, R.; Netzer, R.; Rundfeldt, C. The antiepileptic drug AWD 131 138 stimulated different recombinant isoforms of the rat GABAA receptor through the benzodiazepine binding site. Neuroscience Letters 1998; 245: 85 88

Speciale J, Dayrell Hart B, Steinberg S A. (1991): Clinical evaluation of gamma vinyl gamma aminobutyric acid for control of epilepsy in dogs. J Am Vet Med Assoc.198: 995 1000.

SRENK, P., A. JAGGY, C. CAILLARD, A. BUSATO and P. HORIN (1994): Genetische Grundlagen der Idiopathischen Epilepsie beim Golden Retriever Bern, Univ., Inst. f. Tierneurologie und Inst. f. Tierzucht u. Genetik, Diss.

THOMAS, W. B. (2000): Idiopathic epilepsy in dogs. Vet. Clin. North Am. Small Anim. Pract. 30, 183 206.

VAN DER VELDEN, N. A. (1968): Fits in Tervuren sheeperd dogs: a presumed hereditary trait J. Small Anim. Pract. 9, 63 70

WALLACE, M. E (1973): Keeshonds A genetic study of epilepsy and EEG reading J Small Anim. Pract. 9, 63 70

Yasar, S.; Paronis, C.; Munzar, P.; Tober, C.; Bergman, J. Evaluation of the antiepileptic drug AWD 131 138 for reinforcing and discriminative stimulus effects 1st International Meeting of the Behavioural Pharmacology Society and European Behavioural Pharmacology Society, 1. Apr. 9, 1999, Boston, USA

The invention claimed is:

1. A method for treating a behavioral abnormality in a dog wherein the behavioral abnormality is anxiety, comprising administering to a dog suffering from said anxiety an amount of from 5 to 30 mg/kg of 1-(4-chlorophenyl)-4-(4-morpholinyl)-2,5-dihydro-1H imidazol-1-2-one or a physiological salt thereof once daily to alleviate said anxiety.

2. A method for treating a behavioral abnormality in a dog wherein the behavioral abnormality is anxiety, comprising administering to a dog suffering from said anxiety an amount of from 5 to 30 mg/kg of 1-(4-chlorophenyl)-4-(4- morpholinyl)-2,5-dihydro-1H imidazol-1-2-one or a physiological salt thereof twice daily to alleviate said anxiety.

3. A method for treating a behavioral abnormality in a dog wherein the behavioral abnormality is anxiety, comprising administering to a dog suffering from said anxiety an amount of from 5 to 30 mg/kg of 1-(4-chlorophenyl)-4-(4-morpholinyl)-2,5-dihydro-1H imidazol-1-2-one or a physiological salt thereof once or twice daily to alleviate said anxiety.

\* \* \* \* \*